(12) United States Patent
Chun et al.

(10) Patent No.: US 8,272,866 B2
(45) Date of Patent: Sep. 25, 2012

(54) REMOVABLE ORTHODONTIC APPLIANCE

(76) Inventors: James Jiwen Chun, Raleigh, NC (US); Angela Soyoung Chun, Raleigh, NC (US); Jennifer Miseong Chun, Raleigh, NC (US)

(*) Notice: Subject to any disclaimer, the term of this patent is extended or adjusted under 35 U.S.C. 154(b) by 294 days.

(21) Appl. No.: 12/626,693

(22) Filed: Nov. 27, 2009

(65) Prior Publication Data
US 2011/0129786 A1    Jun. 2, 2011

(51) Int. Cl.
*A61C 7/00* (2006.01)
(52) U.S. Cl. .......................................................... 433/6
(58) Field of Classification Search ................ 433/6, 24; 128/859, 861, 862
See application file for complete search history.

(56) References Cited

U.S. PATENT DOCUMENTS

| | | | | |
|---|---|---|---|---|
| 3,768,164 A | * | 10/1973 | Breads | 433/213 |
| 4,055,895 A | * | 11/1977 | Huge | 433/6 |
| 4,793,803 A | * | 12/1988 | Martz | 433/6 |
| 4,798,534 A | * | 1/1989 | Breads | 433/6 |
| 4,799,884 A | | 1/1989 | Bergersen | |
| 4,892,478 A | * | 1/1990 | Tateosian et al. | 433/6 |
| 5,145,364 A | * | 9/1992 | Martz et al. | 433/6 |
| 5,203,695 A | | 4/1993 | Bergersen | |
| 5,401,168 A | * | 3/1995 | Magill | 433/18 |
| 5,415,542 A | * | 5/1995 | Kesling | 433/6 |
| 6,790,036 B2 | | 9/2004 | Graham | |
| 7,121,825 B2 | | 10/2006 | Chishti et al. | |
| 7,637,262 B2 | * | 12/2009 | Bailey | 128/848 |
| 2002/0192617 A1 | | 12/2002 | Phan et al. | |
| 2003/0224311 A1 | * | 12/2003 | Cronauer | 433/6 |
| 2004/0009449 A1 | | 1/2004 | Mah et al. | |
| 2005/0003318 A1 | * | 1/2005 | Choi et al. | 433/6 |
| 2007/0087300 A1 | | 4/2007 | Willison et al. | |
| 2010/0279245 A1 | * | 11/2010 | Navarro | 433/6 |

* cited by examiner

*Primary Examiner* — Ralph Lewis
(74) *Attorney, Agent, or Firm* — Ash Tankha; Lipton, Weinberger & Husick (57) ABSTRACT

A removable orthodontic appliance and methods of use and manufacturing of the removable orthodontic appliance for repositioning teeth of an upper jaw or lower jaw are provided. The removable orthodontic appliance comprises a trough shaped arch tray that defines an interstitial space between the sides of the arch tray for accommodating the teeth. The arch tray form fits over the contours of the teeth of the upper jaw or lower jaw from a first molar region through a second molar region. The arch tray extends down the teeth on a labial surface and a lingual surface of the teeth to the gingival areas. One or more arch wires are infused and rigidly anchored within the lingual side of the arch tray. Each of the arch wires comprises a surface pre-infused with a polymeric material for rigidly bonding to the lingual side of the arch tray.

17 Claims, 11 Drawing Sheets

REMOVABLE ORTHODONTIC APPLIANCE

BACKGROUND

Orthodontic treatment involves repositioning misaligned teeth to provide an improved appearance, bite relation, and masticating function. Repositioning teeth is accomplished by applying precision-controlled external forces to the teeth over a period of time. Orthodontists typically use one of the two types of dental appliances to exert forces on the teeth, namely fixed appliances and removable appliances.

Fixed appliances consist of brackets, bands, arch wires, and accompanying ligatures or elastomeric rings. The brackets are bonded to the surface of the teeth. Ligatures or elastomeric rings are used to fix the arch wires to the brackets. The primary forces used to induce teeth movement are applied through the arch wires. Periodic adjustments and alterations of arch wires are needed to upgrade the precision and strength of the fixed appliance. Although conventional fixed appliances are effective, they are inconvenient to the patient for several reasons. For example, fixed appliances are usually uncomfortable and unattractive as the arch wires are visible during casual interaction. Moreover, with fixed appliances, maintaining normal oral hygiene is difficult, and improper maintenance can lead to various oral diseases.

In order to avoid visible placement of arch wires on the facial surface of the teeth, the arch wires are sometimes placed on the lingual side of the teeth. Although some progress has been made with lingual placement of the arch wires, the small inter-bracket span, the inaccessibility, and the difficulty to adjust the arch wires make its use complicated. Thus, the lingual placement is mostly used in simple and limited cases that involve minor tooth movement.

Removable appliances offer an alternative to the traditional fixed appliances. Minimal visibility during casual interactions is one of the main benefits of removable appliances. Patients generally prefer removable appliances over fixed appliances, because fixed appliances are considered unsightly and are mostly used for adolescences. Earlier versions of removable appliances utilized loops, finger extensions and hooks to anchor the teeth, while exerting pressure on the teeth through contacting surfaces. Recently proposed removable appliances use plastic retainers with finger springs embedded on the lingual side of the teeth surface. These appliances may not be a viable option for patients who need major teeth movement.

In a different approach, systems and methods have been developed using rigid plastic positioning appliances that cover the entire teeth surface. A series of retainers are used to gradually move the teeth to the desired position. The force required to move the teeth relies on the stiffness of the retainer. Several methods have been proposed to use computer software to generate a three-dimensional model of a patient's dentition and subsequently predict the course of treatment based on the model. However, the computerized prediction is not always accurate, because the variableness of teeth movement in the entire arch cannot be accurately determined with one impression alone. Moreover, the skeletal and dental growth of adolescences is generally unpredictable. As a result, the patient may need to undergo a "refinement" procedure at an additional cost, even though the effectiveness of the refinement procedure is uncertain. Furthermore, the removable appliances may not always fit the patient's mouth properly, causing pain or discomfort. This discomfort is often misconstrued for the effectiveness of the appliance. This method has yet to be widely used due to lack of effectiveness and the high cost involved in the process.

Therefore, there is a need for a method and appliance in the orthodontic field for repositioning teeth that is comfortable to use, aesthetic, and provides effective orthodontic therapy, while reducing the amount of laboratory work required and the cost associated with expensive computer software.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

A removable orthodontic appliance, a method of use, and a method for manufacturing the removable orthodontic appliance for repositioning teeth of an upper jaw or a lower jaw are provided. The removable orthodontic appliance comprises a trough shaped arch tray that defines an interstitial space between the substantially parallel sides of the arch tray for accommodating the teeth of an upper jaw or a lower jaw. In an embodiment, the arch tray is made of a transparent and resilient material. The arch tray removably form fits over and encloses the teeth on the labial surface and the lingual surface of the teeth and extends down to the gums on both sides of the teeth. The arch tray runs along the teeth on the lower jaw and the teeth on the upper jaw and extends from one end molar to the other end molar. One or more arch wires are infused and rigidly anchored within the lingual side of the arch tray. The arch wires are made of a rigid material. Each of the arch wires comprises a surface pre-infused with a polymeric material for rigidly bonding each of the arch wires to the lingual side of the arch tray. The infused arch wires in the arch tray produce one or more predetermined resultant pressures or stresses on the teeth of the upper jaw or the lower jaw for repositioning the teeth. The removable orthodontic appliance utilizes arch wires, for example, to pressure teeth into straighter alignment or to produce desired movement of the teeth.

The arch tray extends to and form fits over the gingival areas of the teeth near the undercut area, and engages the gingival ridges of the upper jaw or the lower jaw. This provides an anchorage for the removable orthodontic appliance that allows the arch wires to produce active forces to move the teeth in the direction dictated by the treatment plan of the orthodontist. The removable orthodontic appliance combines the effectiveness and precision of a conventional fixed appliance with the comfort and convenience of a removable appliance to produce an effective and comfortable system for straightening teeth. Unlike other removable appliances, the forces to reposition the teeth are primarily provided by the arch wires.

In an embodiment, one or more mini brackets secure the arch wires to the arch tray in arch wire-mini bracket arrangements, when the arch wire-mini bracket arrangements are infused within the lingual side of the arch tray. Each of the mini brackets defines a frame and a clamping slot protruding from the frame. Each clamping slot rigidly secures the arch wires to the mini bracket to form the arch wire-mini bracket arrangement. The arch wire-mini bracket arrangement is pre-infused with the polymeric material and infused within the lingual side of the arch tray. The frame comprises one or more windows spaced apart from each other. When the arch wire-mini bracket arrangement is pre-infused with the polymeric material, the polymeric material permeates the windows of each mini bracket through and through.

The arch wires are subjected to a surface treatment for obtaining a predefined surface texture for effective retention of the pre-infused polymeric material over the arch wires. The arch wires have, for example, a rectangular cross-section. The arch tray is molded from a resilient thermoplastic material using a model of a patient's teeth. The arch tray is molded for different sizes and shapes of the jaw.

As comfort to the patient is a major factor involving removable appliances, the arch tray of the removable orthodontic appliance is made of a resilient elastomeric material, for example, thermo setting copolymers that have elastomeric properties to prevent any gingival irritation a patient may experience. The softness of the arch tray provides for a comfortable and good fit on tooth surfaces, without error-induced interferences that may prevent a good fit from being attained. Owing to the comfort, aesthetics, and the accurate orthodontic therapy provided by the orthodontic appliance, patients can be expected to follow the prescription of their orthodontists diligently and hence obtain more predictable results from the treatment.

A method for repositioning teeth of an upper jaw or a lower jaw of a patient is also provided. One or more removable orthodontic appliances are provided, wherein each removable orthodontic appliance progressively repositions the teeth from a first position to one or more intermediate positions and/or to a final position. The final removable orthodontic appliance can be used by the patient as a retainer. In an embodiment, each removable orthodontic appliance is made from a material more rigid than the material of a previous removable orthodontic appliance used in the course of treatment.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1:
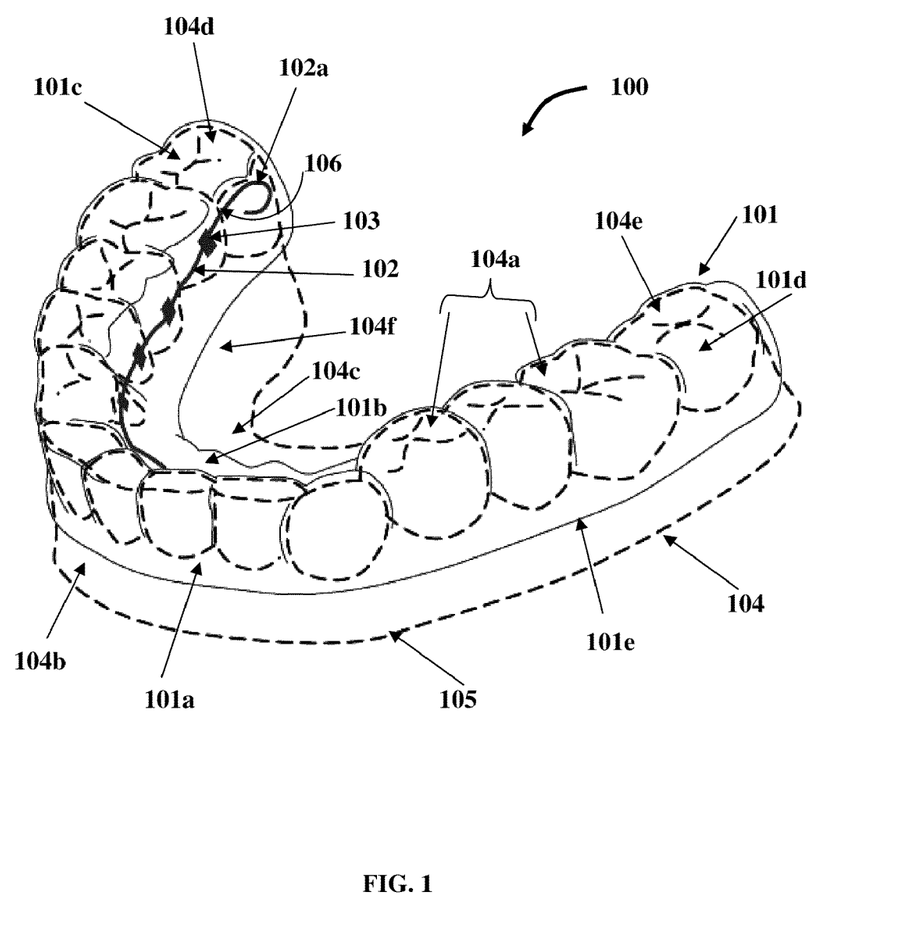
FIG. 1 illustrates a perspective view of a removable orthodontic appliance for repositioning teeth of an upper jaw or a lower jaw in relation to a teeth model.
Figure 2:
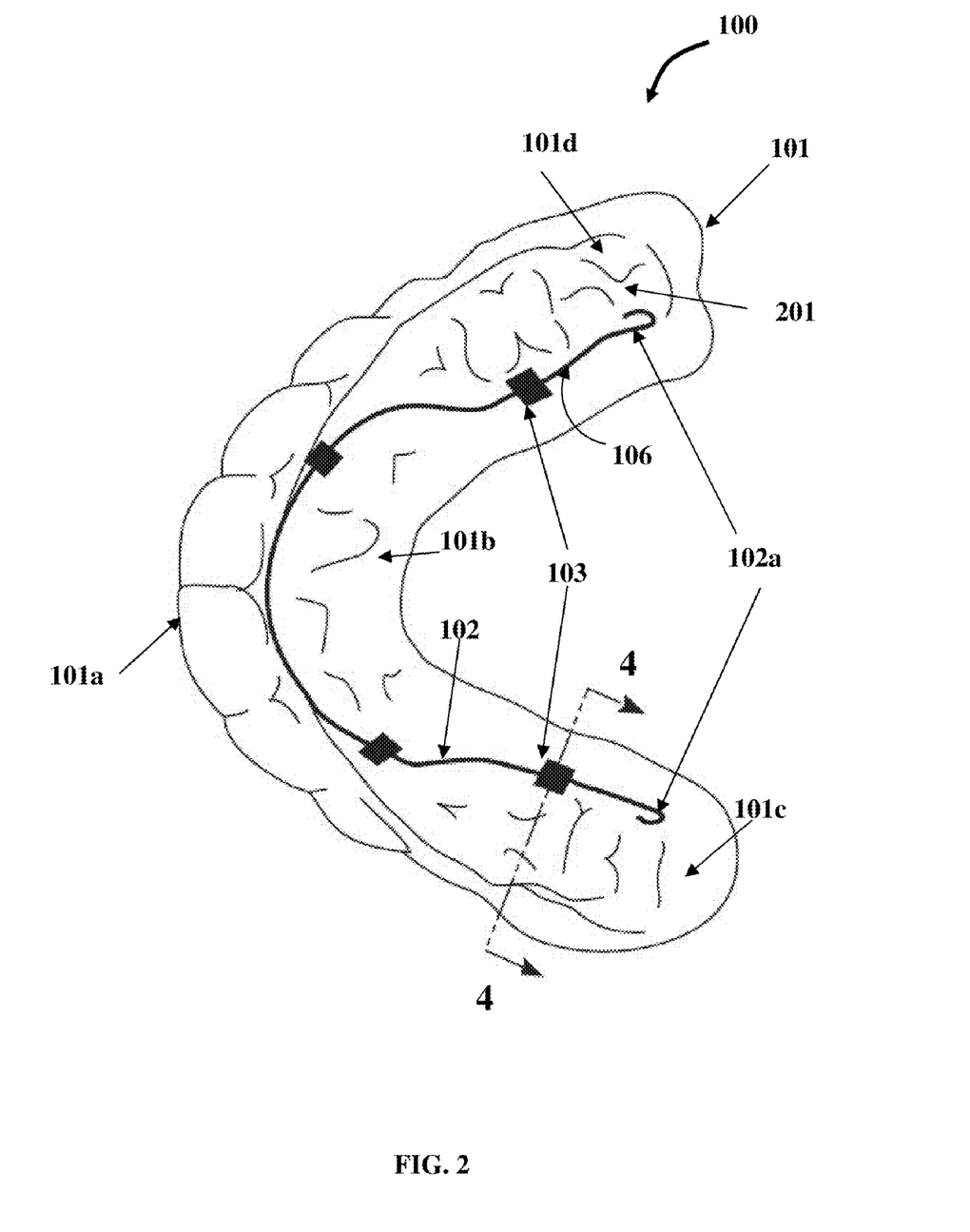
FIG. 2 exemplarily illustrates a bottom perspective view of a removable orthodontic appliance.

FIG. 1 illustrates a perspective view of a removable orthodontic appliance 100 for repositioning teeth 104a of an upper jaw or a lower jaw, herein also referred to as a "jaw" 105 in relation to a teeth model 104. As used herein, the term "removable orthodontic appliance" refers to an orthodontic appliance 100 for repositioning teeth 104a that provides patients with the choice and freedom to remove the orthodontic appliance 100 during occasions such as brushing their teeth, consuming food, etc., without the supervision or assistance of an orthodontist. FIG. 2 exemplarily illustrates a bottom perspective view of the removable orthodontic appliance 100.

As illustrated in FIG. 1 and FIG. 2, the removable orthodontic appliance 100 comprises a trough shaped arch tray 101, herein referred to as an "arch tray", that defines an interstitial space between the substantially vertical sides 101a and 101b of the arch tray 101 for accommodating the teeth 104a of an upper jaw or a lower jaw 105. The arch tray 101 removably form fits over and encloses the teeth 104a over the crown and the labial surface 104b and the lingual surface 104c of the teeth 104a. The arch tray 101 extends down the teeth 104a on the lingual surface 104c and the labial surface 104b of the teeth 104a to gingival areas 104f on the jaw 105. The arch tray 101 extends down to the gums 104f up to the gum line 101e on either side of the teeth 104a. The arch tray 101 extends along the teeth 104a from one end molar to the other end molar, i.e., for the lower jaw 105 from a first molar region 101c through a second molar region 101d, as illustrated in FIG. 1. Similarly, the arch tray 101 extends along the teeth 104a from one end molar to the other end molar on the upper jaw 105. In an embodiment, the arch tray 101 is made of a transparent and resilient polymeric material, for example, polyester or ethylene vinyl acetate (EVA). As used herein, a "labial side" 101a is the side of the arch tray 101 that is disposed proximal to the lip of the patient or on the labial surface 104b of the teeth 104a when the removable orthodontic appliance 100 is fitted onto the patient's dentition. Also, as used herein, a "lingual side" 101b is the side of the arch tray 101 that is disposed proximal to the tongue of the patient or on the lingual surface 104c of the teeth 104a when the removable orthodontic appliance 100 is form fitted onto the patient's dentition. The first molar region 101c and the second molar region 101d, for example, correspond to the right molar region 104d and the left molar region 104e of a teeth model 104. In the form fit position, the arch tray 101 provides, for example, in some occasions, passive retention of the removable orthodontic appliance 100 around the teeth 104a.

As illustrated in FIG. 1 and FIG. 2, one or more arch wires 102 are infused and rigidly anchored within the lingual side 101b of the arch tray 101. In an embodiment, the arch wire 102 is completely infused within the lingual side 101b of the arch tray 101. In another embodiment, the arch wire 102 is partially infused within the lingual side 101b of the arch tray 101 at one or more infusion points 106. The arch wires 102 are made of a rigid material, for example, a metal alloy. Each of the arch wires 102 comprises a surface pre-infused with a polymeric material for rigidly bonding to the lingual side 101b of the arch tray 101. The infused arch wires 102 of the arch tray 101 produces one or more predetermined resultant pressures or stresses on the teeth 104a of the jaw 105 for repositioning the teeth 104a. In an embodiment, one or more mini brackets 103 secure the arch wires 102 to the mini brackets 103 within the lingual side 101b of the arch tray 101. The arch wire 102 is curved at the ends 102a to prevent the ends 102a of the arch wire 102 from undesirably protruding out of the arch tray 101.

Figure 3:
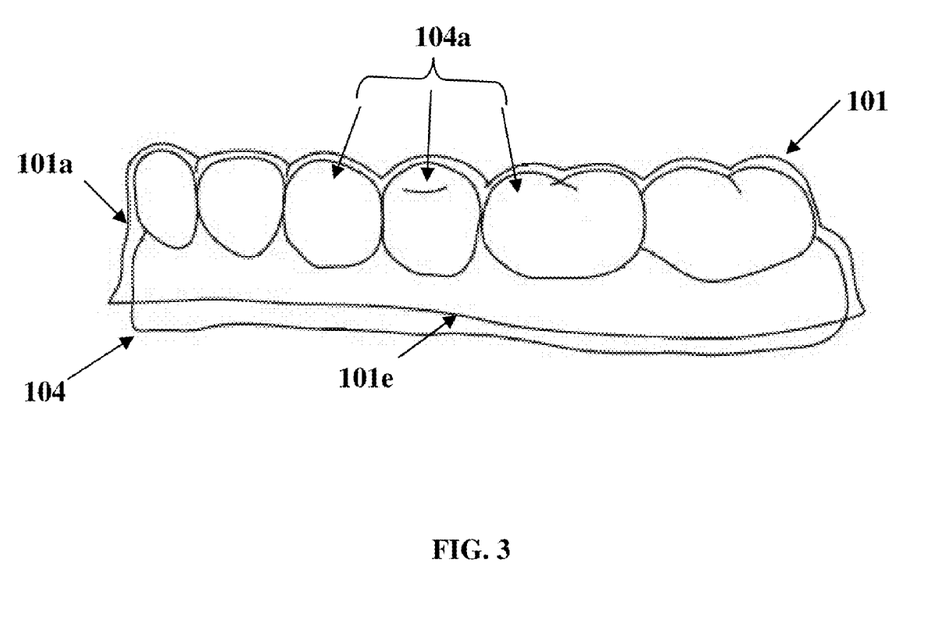
FIG. 3 exemplarily illustrates a side orthogonal view of the removable orthodontic appliance when the removable orthodontic appliance is form fitted over the teeth of an upper jaw or a lower jaw.
Figure 4:
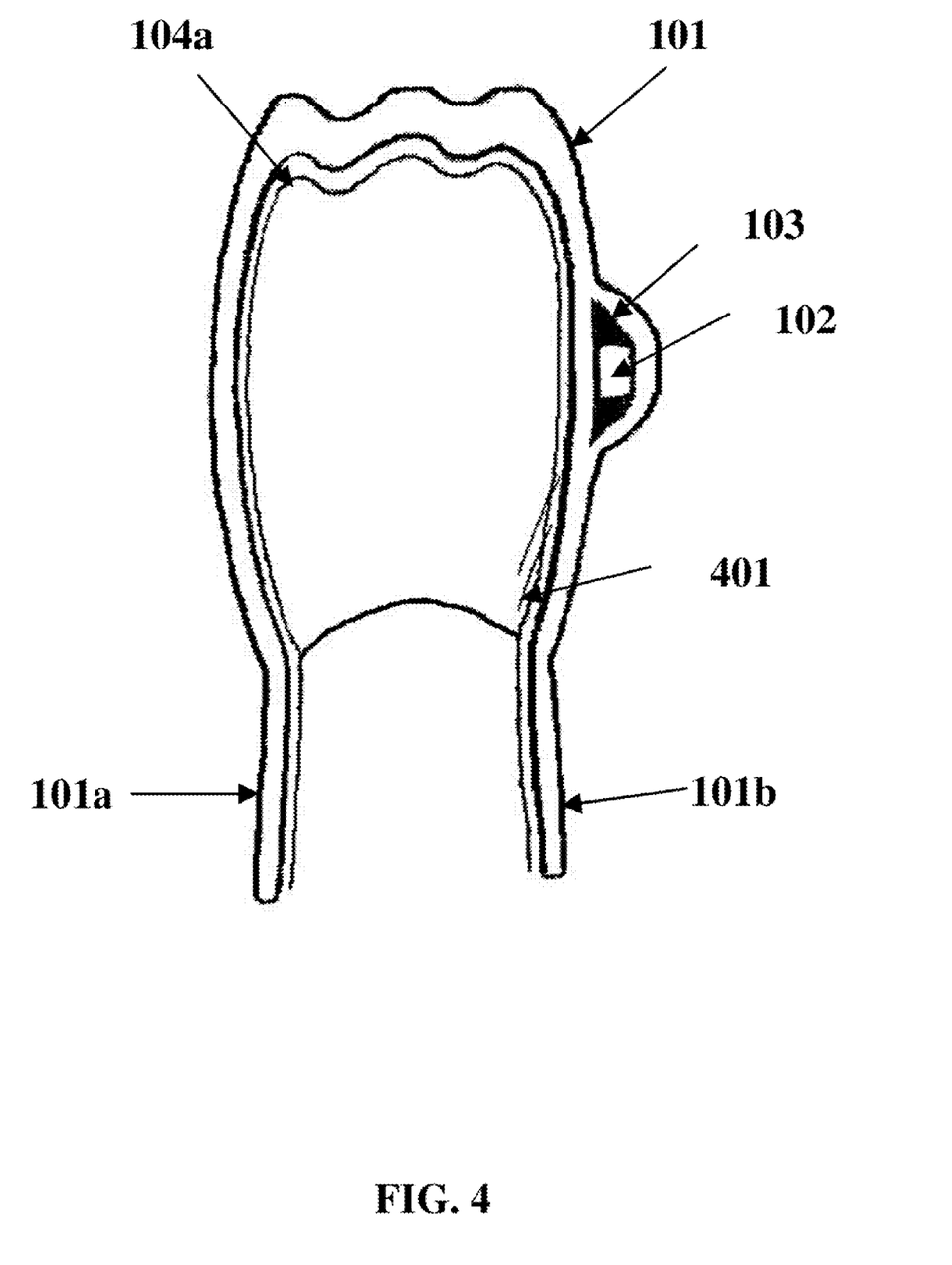
FIG. 4 exemplarily illustrates a sectional view of the removable orthodontic appliance when the orthodontic appliance is form fitted over the teeth of an upper jaw or a lower jaw.

FIG. 3 exemplarily illustrates a side orthogonal view of the removable orthodontic appliance 100 when the removable orthodontic appliance 100 is form fitted over the teeth 104a of the jaw 105. As illustrated in FIGS. 3 and 4, the arch tray 101 extends to and form fits over the entire coronal portion of the teeth 104a, and extends down the lingual and labial surfaces 104b and 104c of the teeth 104a to a part of the undercut areas 401 near the gingival area 104f of the teeth 104a, and engages the gingival ridges of the jaw 105. The close fit of the arch tray 101 to the contours of the teeth 104a, especially onto the part of the undercut area 401, allows the arch tray 101 to firmly cling to the teeth 104a. The anchorage provided by this form fit of the arch tray 101 over the teeth 104a through the gingival area allows the arch wires 102 to exert pressure on the teeth 104a in the direction as required by the treatment plan of the orthodontist. The resilient nature of the arch tray 101 allows the removable orthodontic appliance 100 to stretch and fit onto the teeth 104a over the undercut area 401. The entire removable orthodontic appliance 100 can be lifted off the jaw 105 with sufficient lift force from an edge of the arch tray 101.

FIG. 4 exemplarily illustrates a sectional view along the line 4-4 in FIG. 2 when the removable orthodontic appliance 100 is form fitted over the teeth 104a of the jaw 105. The arch tray 101 extends down on either side of the teeth 104a on the labial side 101a and the lingual side 101b of the arch tray 101. The arch wire 102 and the mini brackets 103 are infused on the lingual side 101b of the arch tray 101.

Figure 5A:
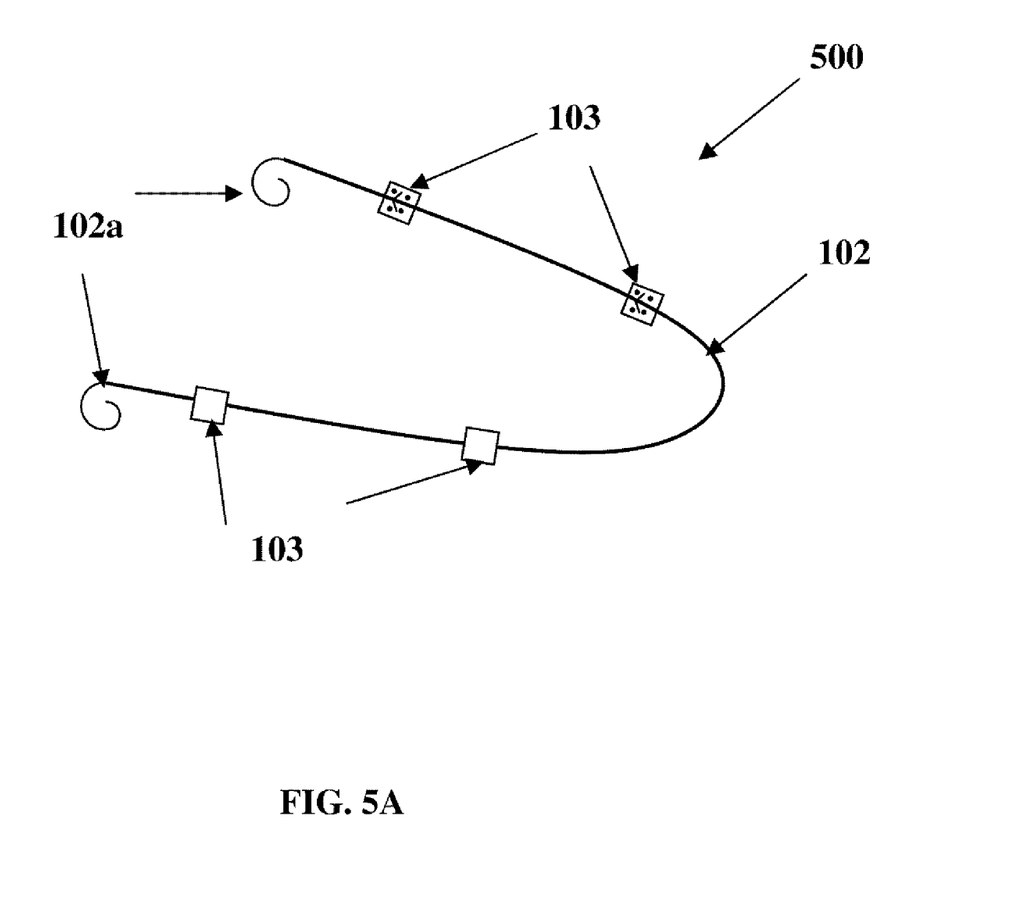
FIG. 5A exemplary illustrates an arch wire-bracket arrangement of the removable orthodontic appliance.

As illustrated in FIG. 5A, in an embodiment, one or more mini brackets 103 secure the arch wires 102 to the mini brackets 103 to form an arch wire-mini bracket arrangement 500. FIG. 5A exemplary illustrates the arch wire-bracket arrangement 500 of the removable orthodontic appliance 100.

Figure 5B:
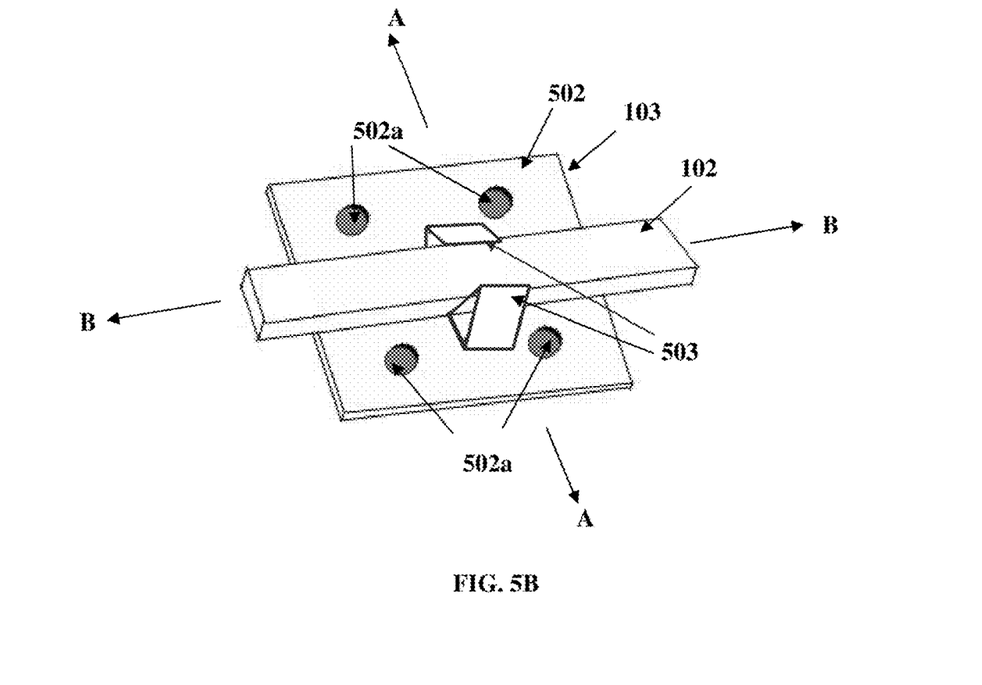
FIG. 5B exemplarily illustrates an enlarged view of the arch wire-bracket arrangement showing the arch wire secured to a mini bracket.
Figure 5C:
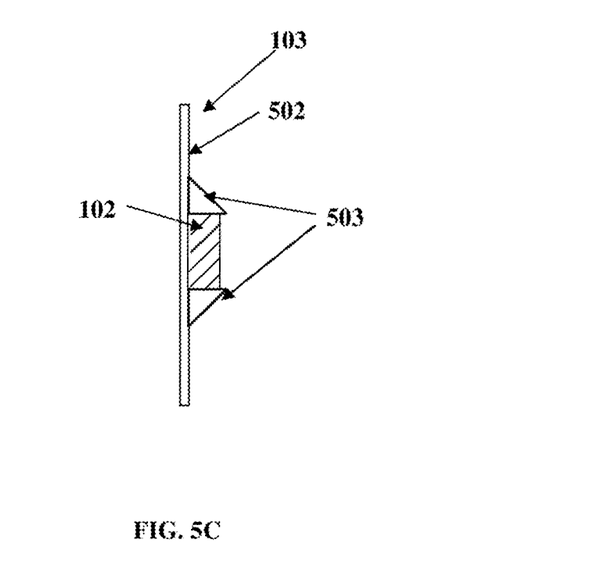
FIG. 5C exemplarily illustrates an enlarged sectional view of the arch wire-bracket arrangement.

FIG. 5B exemplarily illustrates an enlarged view of the arch wire-mini bracket arrangement 500 showing the arch wire 102 secured to mini brackets 103. As illustrated in FIG. 5B, each of the mini brackets 103 defines a frame 502 and a clamping slot 503 protruding from the frame 502. Each clamping slot 503 secures the arch wires 102 to the mini bracket 103 to form the arch wire-mini bracket arrangement 500, which is then infused within the lingual side 101b of the arch tray 101 as illustrated in FIG. 1. The clamping slot 503 can have different shapes, for example, a rectangular shape, to rigidly secure the arch wires 102 to clamping slot 503. The frame 502 comprises one or more windows 502a spaced apart from each other. When the arch wire-mini bracket arrangement 500 is pre-infused with the polymeric material, the polymeric material permeates the windows 502a of each mini bracket 103. FIG. 5C exemplarily illustrates an enlarged sectional view of the arch wire-bracket arrangement 500. In an embodiment, the arch wire 102 or the arch wire-mini bracket arrangement 500 is completely infused within the lingual side 101b of the arch tray 101. In another embodiment, the arch wire 102 or the arch wire-mini bracket arrangement 500 is partially infused within the lingual side 101b of the arch tray 101.

The removable orthodontic appliance 100 is designed to produce light but sustained pressure on the teeth 104a. Due to the continuous application of pressure through the plastic medium of the arch tray 101 on the teeth 104a, the removable orthodontic appliance 100 minimizes uneven and sudden pressure on the teeth 104a. The removable orthodontic appliance 100 modulates the pressure and delivers a continuous and low to moderate pressure from the arch wires 102 to the teeth 104a. The resilient medium of the arch tray 101 provides an elastic force to move the teeth 104a along the arch wire 102.

The arch wire 102 is selected by the prescription of the orthodontist. The general arch shape of the arch wire 102 is configured to align near the mid-line of the lingual surface 104c of the teeth 104a with the arch wire 102 infused in the arch tray 101 and the removable orthodontic appliance 100 form fitted over the teeth 104a. The arch wire 102 is curved in a circular pattern at the ends 102a to prevent the ends 102a of the arch wire 102 from undesirably protruding out of the arch tray 101. The arch-form and types of arch wires 102 can be fabricated according to conventional criteria for fixed appliance therapy. Arch wires 102 with rectangular or circular cross-sections are used in the removable orthodontic appliance 100. Rectangular arch wires 102 guide the alignment of the teeth 104a along the arch wires 102 for tipping, extrusion, intrusion, and other bodily movements, for example, translation of the teeth 104a along the arch wires 102. The rectangular arch wires 102 can also rotate the teeth 104a in the mesial-distal plane B-B through the bending force at the mesial-distal edges of the clamping slot 503 for tipping, rotation, etc. as illustrated in FIG. 5A. The arch wires 102 also rotate the teeth 104a perpendicularly in the labial lingual plane A-A through the twisting force or torque from the rectangular arch wires 102 to the clamping slot 503 for moving the teeth 104a along the labial-lingual direction. Also, a harder and thicker arch wire 102 usually exerts a stronger force. If more rigidity is required, more than one infused arch wire 102 is used depending on the prescription of the orthodontist.

Figure 6:
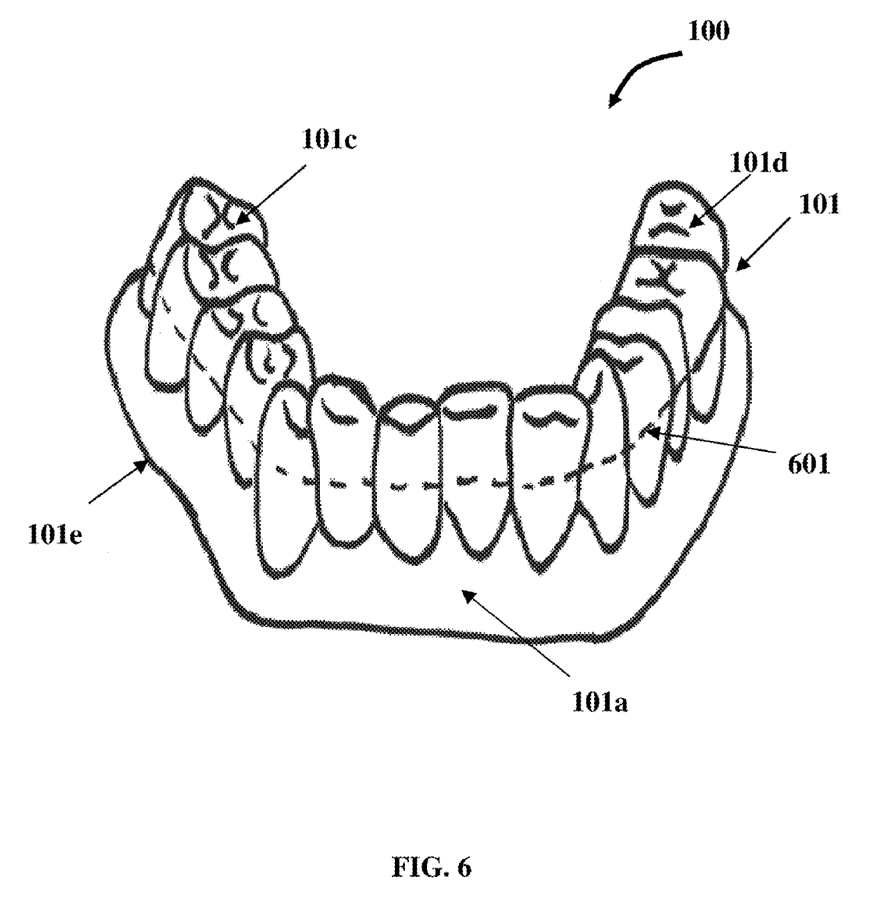
FIG. 6 exemplarily illustrates a front perspective view of a removable orthodontic appliance showing labial infused arch wires.

If greater orthodontic pressure is indicated or prescribed by the orthodontist, facial or labial arch wires 601 that are transparent or with tooth-colored coatings, partially or fully infused within the arch tray 101, can be used together with the lingual arch wires 102. FIG. 6 exemplarily illustrates a front perspective view of the removable orthodontic appliance 100 showing labial infused arch wires 601. The tooth colored arch wires 601 are infused within the labial side 101a of the arch tray 101. With such a variety of choices for the infused arch wires 102 and 601, orthodontists can plan versatile orthodontic treatments formerly possible only with fixed appliances and can choose the amount of pressure they desire.

The material used for fabricating the arch wires 102 is selected by the orthodontist, and comprises, for example, gold, alloys such as stainless steel, cobalt-chromium, beta-titanium, nitinol (A-NiTi), and optical glass. The removable orthodontic appliance 100 can incorporate all the designs of the arch wires 102 currently used by orthodontists in achieving the desired teeth movements. However, slightly stronger arch wires 102 may be preferred due to the internal resistance from the polymeric material of the arch tray 101. The designs of arch wires 102 infused within the arch tray 101 include loops and helices, for example, squashed (butt) loop, closed horizontal loop, open helix (single), open helix (triple), vertical open loop, open horizontal loop, combination loop, omega loop, delta, helical loop, 3-D loop, horizontal "T" open loop, squashed "T" loop, open helical (wide) loop, vertical open (butt) loop, horizontal "L" open helical (boot) loop, vertical-horizontal helix combination, crossed "T" closing loop, double vertical crossed "T" closing loop, etc. The pressure from the removable orthodontic appliance 100 may diminish as the tooth position reaches the target position. If the pressure from the loops and helices in the arch wires 102 begins to decrease during the course of the treatment, the removable orthodontic appliance 100 can be recharged by placing the removable orthodontic appliance 100 back on a recharging cast or the teeth model 104 provided to the patients for a period of time. The removable orthodontic appliance 100 is placed on the teeth model 104 for a predetermined period of time depending on type of arch wires 102 infused within the lingual side 101*b* of the arch tray 101. The recharging casts are configured in a teeth position to restore stress back to the arch wires 102. When the removable orthodontic appliance 100 is placed back on the recharging cast 104, the arch wires 102 are pressured back to or over their original shape and thus recover their original tensile or compressive strength. The recharged removable orthodontic appliance 100 is then re-applied according to the treatment plan of the orthodontist until the removable orthodontic appliance 100 runs its course.

In an embodiment, the arch wire 102 is removably infused within the arch tray 101, for example, by a plastic fusion process, by miniature screws, etc. This embodiment allows the arch wire 102 to be removed from the arch tray 101, reshaped or re-cast as required by the orthodontist and then reattached to the arch tray 101. The arch wires 102 can be infused at one or more infusion points 106 along the lingual side 101*b* of the arch tray 101 by spot welding of plastics of similar or different grades. The arch wires 102 can be removed from the arch tray 101, for example, by a plastic de-fusion process by spot application of heat or by solvents that temporarily dissolve the polymer of the arch tray 101 at room temperature.

In another embodiment, the arch wire 102 comprises several sections of the arch wire 102 that are detachably fused to the arch tray 101. During the orthodontics' procedure, one or more sections of the arch wire 102 can be defused or disconnected from the arch tray 101, and reshaped or manipulated to provide new pressure or pressure points on the misaligned teeth 104*a*.

Figure 7:
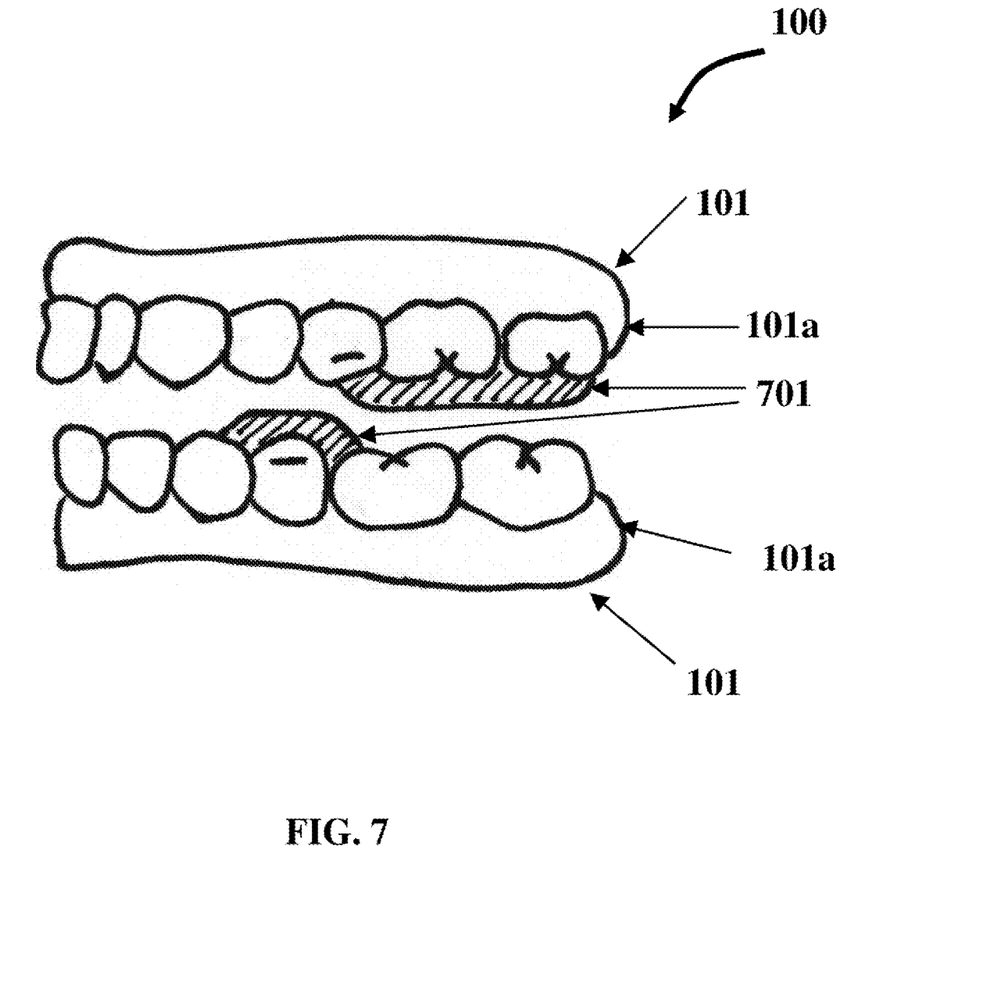
FIG. 7 exemplarily illustrates a side orthogonal view of the removable orthodontic appliance showing occlusal components.

The removable orthodontic appliance 100 precisely positions the teeth 104*a* along their occlusal and incisal edges, instead of merely aligning the teeth 104*a* along the mid line of the labial surface 104*b*. This ensures that the patient has optimal interocclusal relation, while avoiding occlusal interferences. As exemplarily illustrated in FIG. 7, functional and occlusal components 701, for example, occlusal or incisal ramps 701 can be built in the removable orthodontic appliance 100. FIG. 7 exemplarily illustrates a side orthogonal view of the removable orthodontic appliance 100 showing the occlusal components 701 embedded within the arch tray 101. Occlusal or incisal ramps 701 control the eruption of anterior and posterior teeth 104*a*, and open a vertical dimension between the upper and lower jaws 105. For example, specific occlusal components 701 provide stimulus to posture the mandible to a new position.

The removable orthodontic appliance 100 can produce extrusive, rotational, and other directional pressures on targeted teeth 104*a* using specific designs of the arch wires 102. The arch tray 101 extends to the undercut area 401 and the gingival area 104*f* to increase the anchorage of the removable orthodontic appliance 100 to the jaw 105. Adjustments to the removable orthodontic appliance 100 are required to easily insert the removable orthodontic appliance 100 onto the patient's dentition. For example, the undercut areas 401 on the teeth model 104 can be modified to prevent excessive undercut that will prevent the removable orthodontic appliance 100 from fitting in the patient's dentition. Release openings along the gum line 101*e* of the arch tray 101 can be made to allow the removable orthodontic appliance 100 to easily fit onto the patient's dentition.

Unlike other removable appliances, the pressure for moving the teeth 104*a* is primarily provided by the arch wires 102 of the removable orthodontic appliance 100. The elastomeric material of the arch tray 101 form fits around the contours of the teeth 104*a* and the undercut areas 401 when the removable orthodontic appliance 100 is inserted onto the patients' dentition, while the arch wires 102 exert pressure to reposition the teeth 104*a* to the desired position. Since the removable orthodontic appliance 100 holds the teeth 104*a* from all six directions of the dentition, namely, facial, lingual, mesial, distal, incisal and gingival directions, the arch wires 102 can exert pressures from these directions to the teeth 104*a*.

The removable orthodontic appliance 100 only exerts pressure to the target teeth 104*a* that are to be moved, and only in the direction the teeth 104*a* are desired to be moved. Inconsistencies in other rigid removable appliances tend to introduce unexpected interferences that cause discomfort and unwanted movements in the teeth 104*a* that do not require movements. However, due to the resilient nature of the arch tray 101, unnecessary teeth movements do not occur in non-targeted areas of the patient's dentition. As the removable orthodontic appliance 100 stresses the teeth 104*a* from a previous position to a new position, the main orthodontic pressure is derived from the most rigid portion of the removable orthodontic appliance 100, namely, the arch wires 102. The function of the arch tray 101 that covers the teeth 104*a* is to provide passive retention of the removable orthodontic appliance 100 around the entire teeth 104*a*. The resilient material between the arch wires 102 and the inner wall 201 of the arch tray 101 covering the teeth 104*a* acts as an elastic medium that transfers the pressure from the arch wires 102 evenly to the teeth 104*a*. This transfer occurs only in the targeted areas where the tooth position needs to be changed. If a tooth 104*a* is not targeted for repositioning, the arch tray 101 simply fits over the non-targeted area passively and acts mainly as an anchor for other teeth 104*a* that require movement. The arch wire 102 is pre-infused with a polymeric material, for example, polyester or ethylene vinyl acetate (EVA), and infused into the arch tray 101 and is resistant against internal discrepancies or spurious movements, such as translation, rotation, bending, and twisting inside the arch tray 101. These discrepancies would displace the arch wires 102 away from the original position inside the arch tray 101 and create displaced voids inside the arch tray 101. Also, these discrepancies can drastically reduce the efficiency and accuracy of the pressure from the arch wires 102.

This removable orthodontic appliance 100 carries both the effectiveness and precision of a fixed appliance. The greater precision of this removable orthodontic appliance 100 ensures that the teeth 104*a* move in a predictable pattern and do not shift undesirably during treatment. The removable orthodontic appliance 100 can pinpoint the target teeth 104*a*, and do not unnecessarily alter the remaining dentition of the patient. This removable orthodontic appliance 100 can produce extrusive, intrusive, tipping, rotational, translational, torque, and other directional forces. Individual teeth 104*a* have different inclination to the true vertical, and have second or third order torques or bends, in-outs, tips, and angulations. The resilient medium of the arch tray 101 adapts to any surface orientation of the teeth 104*a* and the arch form of the arch wire 102, and only exerts pressure where a misaligned tooth has to be repositioned or realigned. In reaction to the elastic changes due to misaligned teeth 104*a*, the reaction force from the arch tray 101 acts in the direction that moves the teeth 104a to their intended position. Since the plastic medium of the arch tray 101 covers the entire exposed area of the teeth 104a, the removable orthodontic appliance 100 can move the teeth 104a in all possible spatial orientations, namely, up and down for extrusion and intrusion, left and right for mesial and distal movements, and front and back for facial and lingual movements.

The removable orthodontic appliance 100 allows the use of straighter arch wire 102 despite the various thicknesses of individual teeth 104a, and the second order or third order bending of the teeth 104a. Preformed arch wires 102 that follow the arch form may be used with the removable orthodontic appliance 100. In conjunction with the arch wire 102, the removable orthodontic appliance 100 makes it possible to deliver motions such as tipping, rotation, torque, rotation, tipping, translation, intrusion, and extrusion simultaneously. The removable orthodontic appliance 100 makes the clinicians and their lab easily manageable by eliminating the need for first, second, or third order bends in each arch wire 102, and by replacing the routine ligation with the inherent rotational control and elastomeric binding. Thus, removable orthodontic appliance 100 enhances the type of treatment that can be achieved, and hence enables orthodontists to treat a wider variety of orthodontic cases.

Comfort and visibility are key factors in the removable orthodontic appliance 100. The arch tray 101 of the removable orthodontic appliance 100 is made of a resilient material, for example, thermo setting copolymers that have elastomeric properties to prevent any gingival irritation a patient may experience. The visibility of the removable orthodontic appliance 100 can be improved or upgraded through the use of natural-looking painted soft facial veneers-like shading on the arch tray 101.

The orthodontists dictate the direction, the type of movement, and the amount of movement on each tooth, and the functional and occlusal changes of upper or lower jaws 105 in a dental treatment chart recording the phases of treatment. Typically, the treatments are phased in three stages. The first stage focuses on alignment and leveling of teeth 104a with simple and faster movements such as rotation, tipping, etc. The second stage is directed towards closing inter-tooth spaces, which require lower torques and bodily movements. The third stage is for fine tuning and finishing. The orthodontist will reposition the teeth 104a on the teeth model 104 in the laboratory setting based on the treatment phases, map the specific movement of each tooth, plan the occlusal and functional changes, and then fabricate the removable orthodontic appliances 100. The orthodontist may designate a number system on the lingual side 101b of the removable orthodontic appliance 100 indicating the phase and sequence of the removable orthodontic appliances 100.

Figure 8:
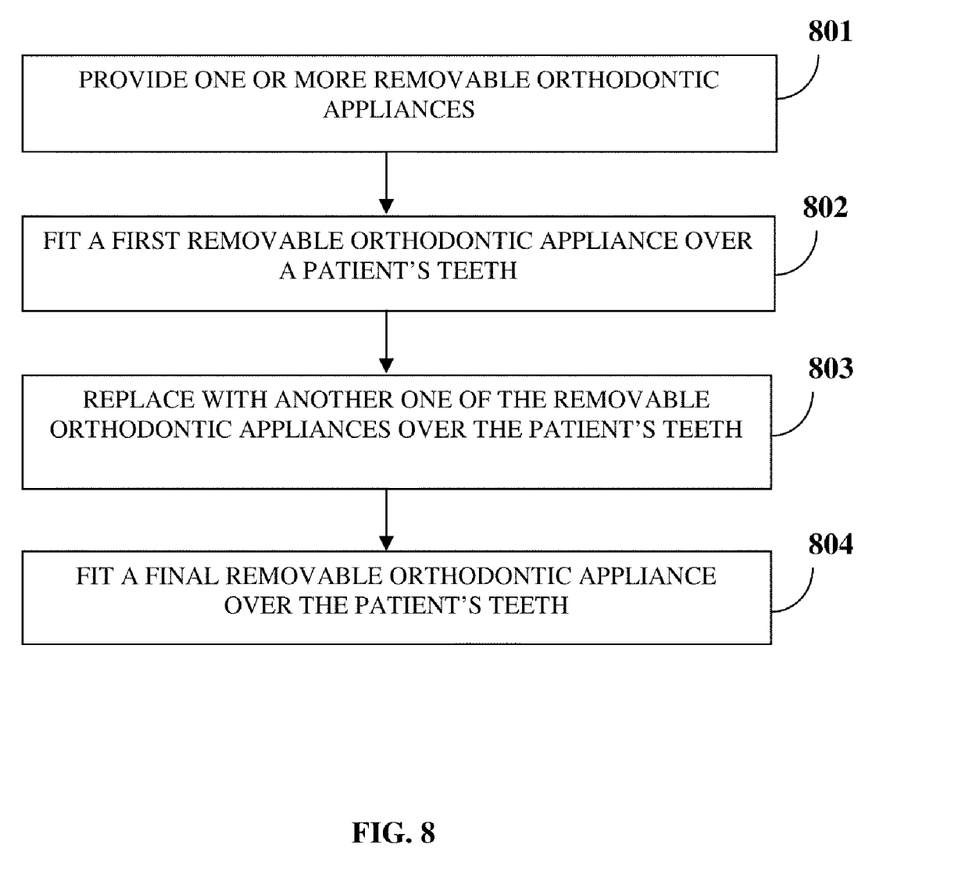
FIG. 8 illustrates a method for repositioning teeth of an upper jaw or a lower jaw of a patient.

FIG. 8 illustrates a method for repositioning teeth 104a of an upper jaw or a lower jaw, herein referred to as the "jaw" 105, of a patient. One or more removable orthodontic appliances 100 as disclosed and illustrated in the detailed description of FIGS. 1-7 are provided 801. Each of the removable orthodontic appliances 100 progressively or incrementally repositions or adjusts teeth 104a from a first position to one or more intermediate positions and/or to a final position. Each removable orthodontic appliance 100 comprises an arch tray 101 and one or more arch wires 102 infused within the lingual side 101b of the arch tray 101. The arch tray 101 of each removable orthodontic appliance 100 form fits over contours of the teeth 104a of the jaw 105 and the gingival areas 104f of the teeth 104a, and engages the gingival ridges of the jaw 105.

A first removable orthodontic appliance 100 is tight fitted 802 over the teeth 104a of the jaw 105 with the form fitting arch tray 101. The tight fit of the removable orthodontic appliance 100 is obtained in part due to the elastomeric properties of the polymeric material used for the arch tray 101 including the inner walls 201 of the arch tray 101. The geometry of the first removable orthodontic appliance 100 is selected to reposition teeth 104a from a first position to an intermediate position or to a final position by the predetermined pressures or stresses produced by the rigidly bonded arch wires 102. Due to the rigid bonding between the arch tray 101 and the arch wire 102 or the arch wire-mini bracket arrangement 500, the pressures produced by the arch wires 102 are effectively transferred to the arch tray 101, which in turn transfers the pressure to the teeth 104a in contact with the arch tray 101. The geometry of the first removable orthodontic appliance 100 is selected based on the model 104 of the teeth 104a in the first position. The first removable orthodontic appliance 100 is replaced 803 with another one of the removable orthodontic appliances 100 over the teeth 104a of the jaw 105 through the form fitting arch tray 101. The geometry of the other removable orthodontic appliances 100 are selected to progressively reposition the teeth 104a through successive intermediate positions by the predetermined pressures produced by the rigidly bonded arch wires 102. The geometry of each of the intermediate removable orthodontic appliances 100 is selected based on the model 104 of the teeth 104a in one of the previous intermediate positions. A final removable orthodontic appliance 100 is tight fitted 804 over the teeth 104a of the jaw 105 with the form fitting arch tray 101. The geometry of the final removable orthodontic appliance 100 is selected to reposition the teeth 104a from one of the intermediate positions to a final position by the predetermined pressures produced by the rigidly bonded arch wires 102. The geometry of the final removable orthodontic appliance 100 is selected based on the model 104 of the teeth 104a in a previous intermediate position.

The method disclosed herein requires an impression of the patient's dentition to be taken at each consultation with the orthodontist. The method for repositioning teeth 104a from an initial arrangement to a sequential arrangement uses a set of removable orthodontic appliances 100. The patterns of teeth movement are designed by repositioning the initial teeth alignment to the desired position on a teeth model 104 in dental laboratory settings. This is accomplished by carefully separating the teeth 104a away from its original position, and reattaching the teeth 104a to the desired position. The type and range or degree of movements are dictated by the orthodontist. The patients may need to periodically visit the orthodontist to monitor the progress of their treatment. Once the initial impression is taken, the first removable orthodontic appliance 100 is fitted over the patient's dentition as disclosed in the detailed description of FIG. 8. The softness and rigidity of each removable orthodontic appliance 100 can be selected by the orthodontist according to the level or amount of force required by the patient. In an embodiment, each removable orthodontic appliance 100 is fabricated from a more rigid material than a previous removable orthodontic appliance 100 in the course of treatment.

The removable orthodontic appliances 100 can be constructed with different types of arch wires 102 varying from soft to hard. The patient can be instructed to try a removable orthodontic appliance 100 with a soft arch wire 102 and advance to the arch wires 102 with higher strength or vice versa. In the method disclosed herein, the orthodontists change from soft arch wires 102 to strong arch wires 102 as the patient builds up tolerance for the arch wires 102. After the first set of removable orthodontic appliances 100 have run their course, a second impression of the teeth 104a is taken, and a new set of removable orthodontic appliances 100 are fabricated to reposition the teeth 104a from the prior incremental position to a new intermediate position. This process is repeated until the desired teeth alignment is achieved. Three-dimensional X-rays are used to predict the proper course of tooth movement and to precisely monitor the movement of the teeth 104a at different stages. The final removable orthodontic appliance 100 is fitted over the patient's dentition. The final removable orthodontic appliance 100 positions the teeth 104a from the last intermediate position to a final position. The method disclosed herein ensures that the removable orthodontic appliance 100 maintains the precision and accuracy of the arch wire 102 throughout the treatment. The final removable orthodontic appliance 100 may be retained over the patient's dentition as a retainer.

Figure 9:
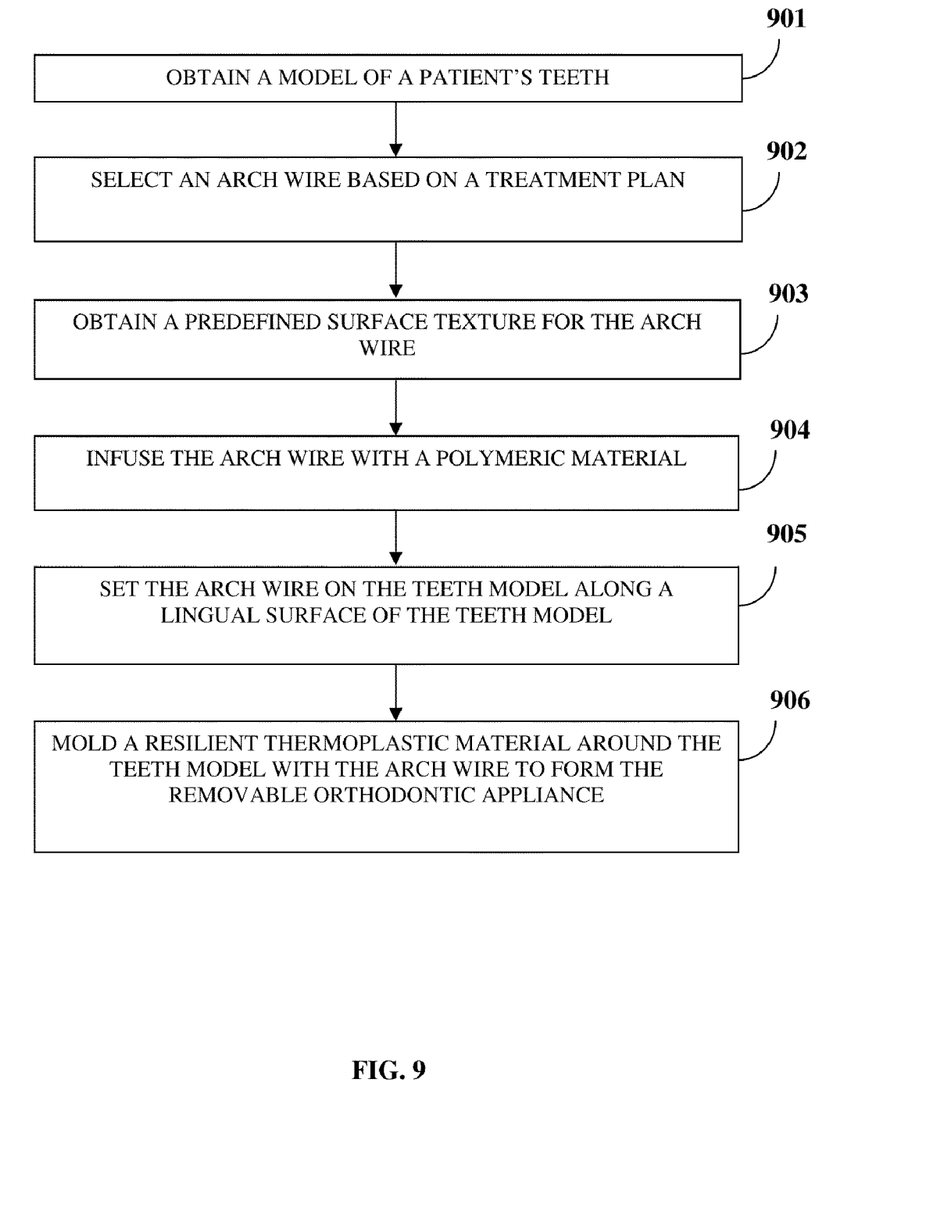
FIG. 9 exemplarily illustrates a method of manufacturing a removable orthodontic appliance for repositioning teeth of an upper jaw or a lower jaw.

FIG. 9 exemplarily illustrates a method of manufacturing a removable orthodontic appliance 100 for repositioning teeth 104a of an upper jaw or a lower jaw 105. A model 104 of the teeth 104a is obtained 901, where the teeth model 104 comprises a labial surface 104b and a lingual surface 104c. An arch wire 102 is selected 902 based on a treatment plan or by prescription of an orthodontist. The arch wire 102 is bent to align with the lingual surface 104c of the teeth model 104 along a midline of the lingual surface 104c.

The arch wire 102 is subjected to a surface treatment for obtaining 903 a predefined surface texture for effective retention of the pre-infused polymeric material over the arch wire 102. If the arch wire-mini bracket arrangement 500 is used, the arch wire-mini bracket arrangement 500 is subjected to a surface treatment for obtaining the predefined surface texture. In an embodiment, the arch wires 102 are sandblasted to obtain 903 the predefined surface texture. In sandblasting, the sand particles used may have different sizes and grades. If the surface of the arch wire 102 or the arch wire-mini bracket arrangement 500 is too hard for sandblasting to be effective, laser etching or chemical etching is used. Laser etching or chemical etching techniques tend to create deeper porous surface structures 1001, as exemplarily illustrated in FIG. 10. The predefined surface texture comprises, for example, a micro or nano porous surface structure 1001 with round-shaped micro or nano pores, large enough to suffuse the micro pores with the molten polymeric material.

Figure 10:
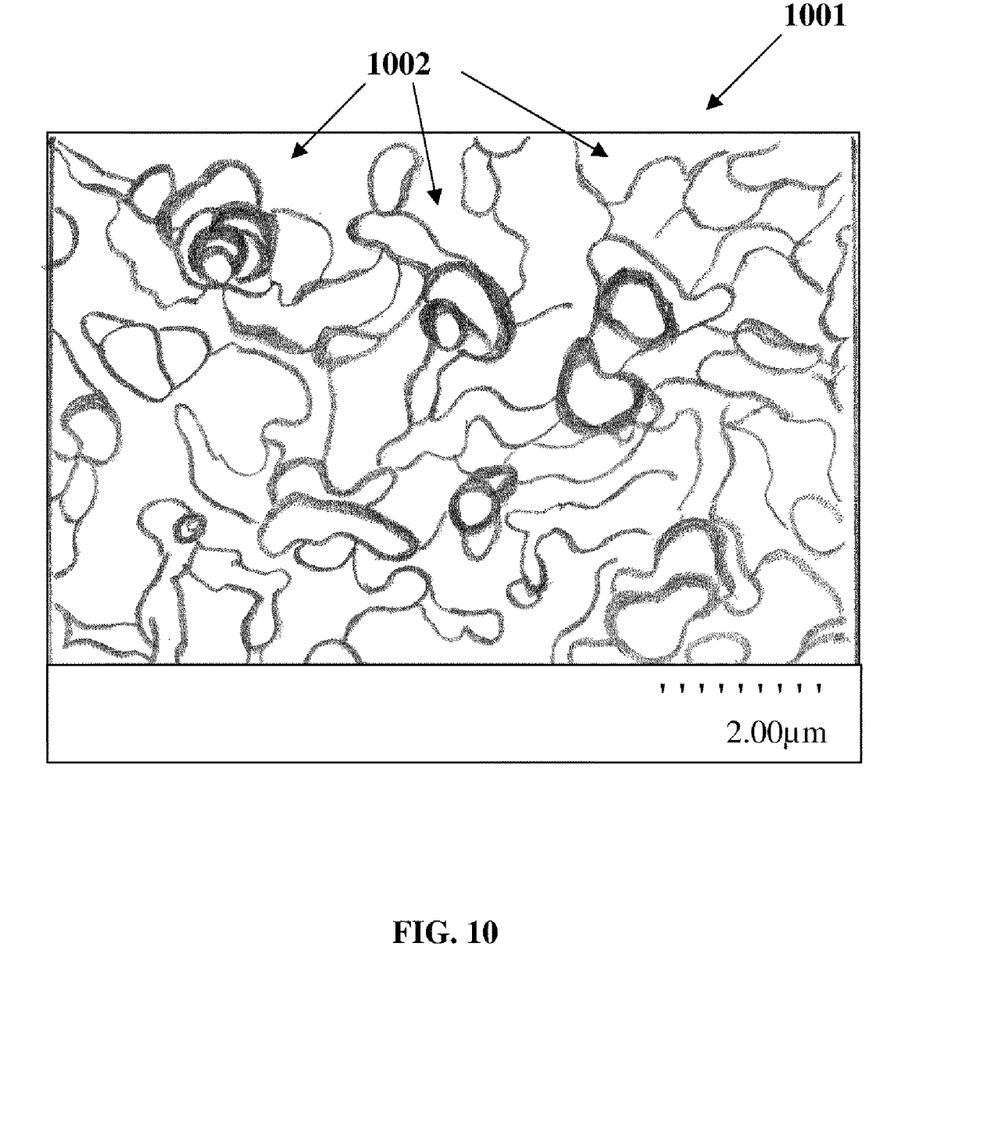
FIG. 10 exemplarily illustrates a microscopic porous surface structure for the arch wire or the arch wire-bracket arrangement.

FIG. 10 exemplarily illustrates the microscopic porous surface structure 1001 of the arch wire 102 and/or the arch wire-bracket arrangement 500. Surface treatment of the arch wire 102 increases the contact area for bonding between the arch wire 102 and the polymeric material. The bonding between the arch wire 102 and the polymeric material is a physical bonding through entanglement of the micro porous surface structures 1001 created by the surface treatment on the arch wire 102 with the polymer fibers melted and infused into the porous space 1002. It is possible that due to the surface treatment, the effective strength of arch wires 102 may be reduced. Thus, wider and stronger arch wires 102 are used to compensate for the loss of strength from the surface treatment.

A technique to allow the polymeric material to suffuse the porous surface structure 1001 is to allow monomers, which make up the polymeric material, to polymerize inside the porous space 1002 using chemical and light activated catalysts that trigger the polymerization, since air bubbles on the micro porous surface structure 1001 may prevent the highly viscous molten polymeric material to flow into the porous space 1002. However, the much smaller and fluid monomers flow more easily into the porous space 1002.

If the arch wire-mini bracket arrangement 500 is used as illustrated in FIGS. 5A-5C, the arch wire-mini bracket arrangement 500 is pre-infused with the polymeric material. The frame 502 of each mini bracket 103 comprises one or more windows 502a or holes spaced apart from each other. When the arch wire-mini bracket arrangement 500 is pre-infused with the polymeric material, the molten polymeric material permeates the windows 502a of each mini bracket 103 through and through. This enhances the bonding of the mini brackets 103 to the polymeric material of the arch tray 101. The windows 502a increase the surface area on the mini brackets 103 for bonding, and allow the polymeric material to anchor the mini brackets 103.

In order to enhance the bonding between the porous surface structure 1001 and the infused polymeric material, a bonding solution containing the monomers and chemical and light activated catalysts is applied on the surface treated arch wires 102. The bonding solution is a self-polymerizing plastic solution. The arch wires 102 are infused 904 with the polymeric material by submerging the monomer-primed surface-etched arch wires 102 in the self-polymerizing plastic solution for a predetermined period of time to allow the polymerizing monomers to flow into the porous space 1002. This ensures that plastic polymer chains are infused into the porous space 1002 of the micro porous surface structure 1001 of the arch wires 102. The arch wires 102 infused with the self-polymerizing plastic solution is set 905 on a teeth model 104 along the lingual surface 104c of the teeth model 104. The arch wire 102 will eventually firmly sit on the teeth model 104 when the molten self-polymerizing solution around the arch wire 102 hardens. In an embodiment, the polymeric materials used are biocompatible and durable.

The arch tray 101 of the removable orthodontic appliance 100 is molded or formed 906 from a sheet of thermoplastic material, for example, thermo setting copolymer with elastomeric properties around a model 104 of a patient's dentition. The arch tray 101 is molded for different sizes and shapes of the patient's dentition. At this stage, soft resilient material representing such components as occlusal and incisal ramps 701 can be added to the upper and lower jaws 105, as illustrated in FIG. 7, by positioning the ramps 701 on the teeth model 104. During treatment, the ramp 701 guides, for example, the lower teeth 104a to move forward as the upper teeth and the lower teeth 104a are closing together. Although the components 701 have been described herein with reference to the occlusal and incisal ramps, the components 701 are not intended to be limited to the occlusal and incisal ramps; rather, the scope of the components 701 extends to all functionally equivalent structures.

In order to mold the arch tray 101, the sheet of resilient thermo setting copolymer, for example, polyester or ethylene vinyl acetate (EVA) is heated to a predetermined temperature to attain a very pliable state, and stretched on top of the teeth model 104 with the seated arch wire 102 or the arch wire-mini bracket arrangement 500 and the other components 701 under air vacuum created using a vacuum pump. The vacuum pump forces the soft copolymer to flow into the open spaces on the teeth model 104. During this molding process, the soft molten copolymer used for molding and the self-polymerizing plastic pre-infused on the arch wire-mini bracket arrangement 500 can melt with each other and form a strong bond through the entanglement of the molten polymer chains. The polymeric material used for pre-infusing the arch wire-mini bracket arrangement 500 can be chosen according to the prescriptions from the orthodontists to be more durable and stronger compared to the thermo setting copolymer used for the molding process. The arch wire-mini bracket arrangement 500 is thus infused within the molded arch tray 101. The infused arch wires 102 possess fairly strong strength against internal twisting and bending. The mini-brackets 103 greatly increase the bondage between the arch wire 102 and the polymeric material. Also, since the arch tray 101 is molded around the teeth model 104, the inner walls 201 of the trough shaped arch tray 101 adopt the surface contours of the teeth model 104.

As the polymeric material cools down to form the arch tray 101 with the infused arch wire-mini bracket arrangement 500, the molded arch tray 101 can be removed from the teeth model 104 and trimmed off below the gum line 101e. Touch flame is usually used to smooth off the sharp contours and edges in the molded arch tray 101. During the course of the treatment, as the patient wears the removable orthodontic appliance 100, the forces in the arch wires 102 may eventually begin to lose their strength. The removable orthodontic appliance 100 can be recharged by placing the removable orthodontic appliance 100 back on a recharging cast or the teeth model 104 provided to the patient for a predetermined period of time depending on the type of arch wires 102 used in the removable orthodontic appliance 100.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A removable orthodontic appliance for repositioning teeth of one of an upper jaw and a lower jaw of a patient, comprising:
   a trough shaped arch tray, said arch tray defining an interstitial space between a labial side and a lingual side of said arch tray for accommodating said teeth of one of said upper jaw and said lower jaw, wherein said arch tray is positioned to form fit over said teeth from a first molar region through a second molar region, and wherein said arch tray extends down said teeth on a lingual surface and a labial surface of said teeth to gingival areas on one of said upper jaw and said lower jaw;
   one or more arch wires infused and rigidly anchored within said lingual side of said arch tray, said arch wires made of a rigid material, wherein each of said arch wires comprises a surface pre-infused with a polymeric material for rigidly bonding each of said arch wires to said lingual side of said arch tray; and
   one or more mini brackets, each of said one or more mini brackets comprising a clamping slot to rigidly secure said one or more arch wires to said one more mini brackets to form an arch wire-mini bracket arrangement, wherein said arch wire-mini bracket arrangement is pre-infused with said polymeric material and infused within said lingual side of said arch tray;
   whereby said infused arch wires in said arch tray produce one or more predetermined pressures on said teeth of one of said upper jaw and said lower jaw for repositioning said teeth.

2. The removable orthodontic appliance of claim 1, wherein said arch tray form fits over contours of said teeth of one of said upper jaw and said lower jaw and gingival areas of said teeth, and engages gingival ridges of one of said upper jaw and said lower jaw.

3. The removable orthodontic appliance of claim 1, wherein each of said one or more mini brackets defines a frame and said clamping slot protruding from said frame, wherein said frame comprises one or more windows spaced apart from each other, wherein said pre-infused polymeric material permeates said one or more windows.

4. The removable orthodontic appliance of claim 1, wherein said one or more arch wires are sand blasted to obtain a predefined surface texture for retention of said pre-infused polymeric material over said arch wires.

5. The removable orthodontic appliance of claim 1, wherein said arch tray is molded from a thermoplastic elastomeric material using a model of said teeth of said patient.

6. The removable orthodontic appliance of claim 1, wherein said arch tray is molded for different sizes and shapes of said upper jaw and said lower jaw.

7. The removable orthodontic appliance of claim 1, wherein each of said arch wires has one of a circular cross-section and a rectangular cross-section.

8. A method for repositioning teeth of one of an upper jaw and a lower jaw of a patient, comprising:
   providing one or more removable orthodontic appliances, wherein each of said one or more removable orthodontic appliances progressively reposition said teeth from a first position to one of an intermediate position or to a final position, wherein each of said one or more removable orthodontic appliances comprises:
      a trough shaped arch tray, said arch tray defining an interstitial space between a labial side and a lingual side of said arch tray for accommodating said teeth of one of said upper jaw and said lower jaw, wherein said arch tray is positioned to form fit over said teeth from a first molar region through a second molar region, and wherein said arch tray extends down said teeth on a lingual surface and a labial surface of said teeth to gingival areas on one of said upper jaw and said lower jaw; and
      one or more arch wires infused and rigidly anchored within said lingual side of said arch tray, said arch wires made of a rigid material, wherein each of said arch wires comprises a surface pre-infused with a polymeric material for rigidly bonding each of said arch wires to said lingual side of said arch tray;
   securing said one or more arch wires to one more mini brackets to form an arch wire-bracket arrangement, wherein each of said one or more mini brackets comprises a clamping slot to rigidly secure said one or more arch wires to said one or more mini brackets, wherein said arch wire-mini bracket arrangement is pre-infused with said polymeric material and infused within said lingual side of said arch tray;
   fitting a first of said one or more removable orthodontic appliances over said teeth with said form fitting arch tray, wherein a geometry of said first removable orthodontic appliance is selected to reposition said teeth from said first position to one of said intermediate positions and said final position by one or more predetermined pressures produced by said rigidly bonded arch wires, wherein said geometry of said first removable orthodontic appliance is selected based on a model of said teeth in said first position;

replacing said first removable orthodontic appliance with another one of said one or more removable orthodontic appliances over said teeth, wherein a geometry of each of said removable orthodontic appliances is selected to progressively reposition said teeth through said intermediate positions by said one or more predetermined pressures produced by said rigidly bonded arch wires, wherein said geometry of each of said removable orthodontic appliances is selected based on a model of said teeth in one of said intermediate positions; and fitting a final one of said removable orthodontic appliances over said teeth with said form fitting arch tray, wherein a geometry of said final removable orthodontic appliance is selected to reposition said teeth from one of said intermediate positions to said final position by said one or more predetermined pressures produced by said rigidly bonded arch wires, wherein said geometry of said final removable orthodontic appliance is selected based on a model of said teeth in one of said intermediate positions.

9. The method of claim 8, further comprising retaining said final removable orthodontic appliance over said teeth as a retainer.

10. The method of claim 8, wherein a material of each of said removable orthodontic appliances is more rigid than a material of a previous one of said removable orthodontic appliances.

11. The method of claim 8, wherein said arch tray form fits over contours of said teeth of one of said upper jaw and said lower jaw and gingival areas of said teeth, and engages gingival ridges of one of said upper jaw and said lower jaw.

12. The method of claim 8, further comprising infusing one or more tooth colored arch wires within said labial side of said arch tray, wherein said tooth colored arch wires are prescribed by an orthodontist.

13. The method of claim 8, further comprising recharging said one or more removable orthodontic appliances by placing said one or more removable orthodontic appliances on said teeth model for a predetermined period of time depending on type of said one or more arch wires infused within said lingual side of said arch tray.

14. The method of claim 8, further comprising providing functional and occlusal components on one of said labial side and said lingual side of said arch tray, wherein said functional and occlusal components comprise occlusal and incisal ramps.

15. A method of manufacturing a removable orthodontic appliance for repositioning teeth of one of an upper jaw and a lower jaw, comprising:

obtaining a model of said teeth, wherein said teeth model comprises a labial surface and a lingual surface;

selecting one or more arch wires based on a treatment plan, wherein said selected arch wires are bent to align with said lingual surface of said teeth model along a midline of said lingual surface;

obtaining a predefined surface texture for said selected one or more arch wires by subjecting said selected one or more arch wires to sand blasting;

infusing said one or more arch wires with said polymeric material by submerging said one or more arch wires under a molten polymeric material for a predetermined period of time;

setting said infused one or more arch wires on said teeth model along said lingual surface of said teeth model, wherein said one or more arch wires firmly sits on said lingual surface of said teeth model when said molten polymeric material around said infused one or more arch wires hardens;

attaching said one or more arch wires to one or more mini brackets using clamping slots on mini brackets to form an arch wire-bracket arrangement; and and molding a resilient thermoplastic material around said teeth model with said attached one or more arch wires by heating a sheet of said resilient thermoplastic material to a predetermined temperature to form around said teeth model and applying a vacuum, whereby said seated one or more arch wires is infused within said resilient thermoplastic material when said resilient thermoplastic material hardens to form said removable orthodontic appliance.

16. The method of claim 15, wherein said arch wire-bracket arrangement is submerged under said molten polymeric material for said predetermined period of time for infusing said arch wire-bracket arrangement with said polymeric material.

17. The method of claim 15, further comprising providing functional and occlusal components on one of said labial side and said lingual side of said arch tray, wherein said functional and occlusal components comprise occlusal and incisal ramps.

* * * * *